(12) United States Patent
Brinker et al.

(10) Patent No.: US 7,988,793 B2
(45) Date of Patent: *Aug. 2, 2011

(54) WASHING SYSTEM FOR DISSOLUTION VESSELS AND THE LIKE

(75) Inventors: Jeffrey Brinker, North Brunswick, NJ (US); Michael Cai, Old Bridge, NJ (US)

(73) Assignee: Distek, Inc., North Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/639,626

(22) Filed: Dec. 16, 2009

(65) Prior Publication Data

US 2010/0089428 A1    Apr. 15, 2010

Related U.S. Application Data

(63) Continuation of application No. 11/263,531, filed on Oct. 31, 2005, now Pat. No. 7,658,198.

(60) Provisional application No. 60/672,075, filed on Nov. 12, 2004.

(51) Int. Cl.
*B08B 9/00* (2006.01)

(52) U.S. Cl. ............ 134/166 R; 134/167 R; 134/168 R; 134/198; 15/302; 15/304

(58) Field of Classification Search .................. 134/113, 134/166 R, 167 R, 168 R, 192, 197, 198; 215/212, 358; 15/3, 302, 304; 422/81
See application file for complete search history.

(56) References Cited

U.S. PATENT DOCUMENTS

| | | | |
|---|---|---|---|
| 2,243,015 A * | 5/1941 | Patterson | 134/103.1 |
| 3,185,355 A | 5/1965 | Lipman | 222/341 |
| 4,218,198 A * | 8/1980 | Kutik et al. | 417/566 |
| 4,913,179 A | 4/1990 | Engel et al. | 134/113 |
| 5,109,562 A * | 5/1992 | Albrecht | 15/56 |
| 5,158,101 A | 10/1992 | Sakka | 134/167 R |
| 5,286,301 A * | 2/1994 | Albrecht | 134/8 |
| 5,316,218 A | 5/1994 | Bowen | 239/246 |
| 5,497,799 A | 3/1996 | Shenk | 134/167 R |
| 5,794,949 A | 8/1998 | Pierce | 279/46.7 |
| 5,918,813 A * | 7/1999 | Rucker | 239/246 |

OTHER PUBLICATIONS

Office Action dated Mar. 12, 2009 from U.S. Appl. No. 11/263,531.
Final Office Action dated Aug. 26, 2009 from U.S. Appl. No. 11/263,531.
Vankel VK 900 Washing Station Service Manual, Vankel, Mar. 2002, pp. 14, 68, and 69.

* cited by examiner

*Primary Examiner* — Joseph L Perrin
*Assistant Examiner* — Benjamin Osterhout
(74) *Attorney, Agent, or Firm* — Mendelsohn, Drucker & Assoc., P.C.; Kevin M. Drucker; Steve Mendelsohn

(57) ABSTRACT

In one embodiment, a washing system including a nozzle assembly having a nozzle and having formed therein a rinse passageway and a waste passageway. Each passageway has first and second ends. The first end of the waste passageway is adapted to be coupled to a waste pump adapted to remove waste fluid via a waste aperture defining the second end of the waste passageway. The first end of the rinse passageway is adapted to be coupled to a rinse pump adapted to provide rinse fluid via a rinse aperture defining the second end of the rinse passageway. The nozzle is coupled to the rinse aperture and is adapted to rotate and direct flow of the rinse fluid outwardly while rotating.

20 Claims, 8 Drawing Sheets

SECTION A-A

SECTION B-B

SECTION C-C

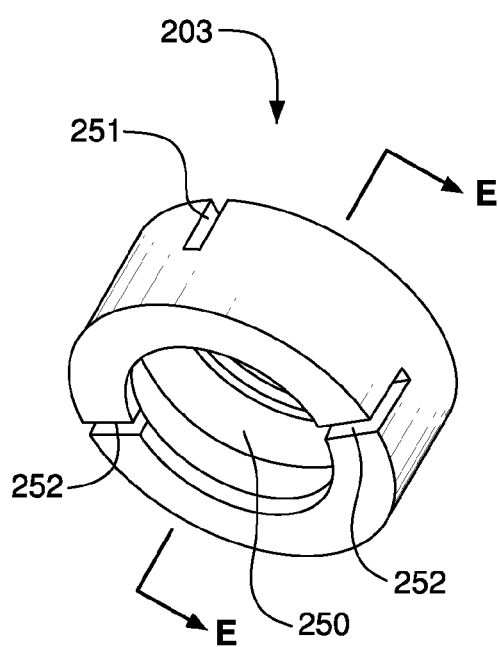
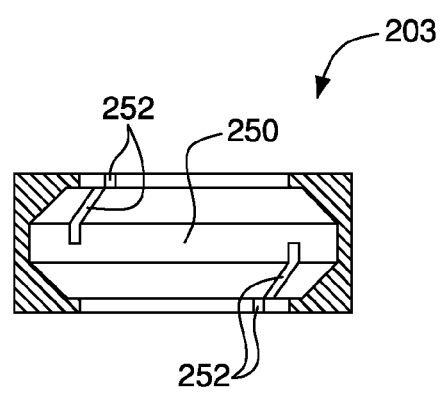
FIG. 8
FIG. 9

US 7,988,793 B2

WASHING SYSTEM FOR DISSOLUTION VESSELS AND THE LIKE

CROSS-REFERENCE TO RELATED APPLICATIONS

This application is a continuation of co-pending U.S. application Ser. No. 11/263,531, filed on Oct. 31, 2005, which claims the benefit of the filing date of co-pending U.S. provisional application No. 60/627,075, filed on Nov. 12, 2004, the teachings of both of which are incorporated herein by reference.

BACKGROUND OF THE INVENTION

1. Field of the Invention

The present invention relates generally to dissolution test equipment, and more particularly, to the washing of dissolution vessels that are used in a dissolution testing system.

2. Description of the Related Art

Drug dissolution, i.e., the rate of drug release from bulk powder or a finished drug product into the human body, is becoming an increasingly important aspect of the biopharmaceutical equation, particularly with the advent of controlled-release dosage forms and the increasing use of poorly-soluble and water-insoluble drugs. Through the use of experimentally-determined drug and drug product in-vitro characteristics, such as solubility and dissolution, it is possible to predict the in-vivo performance for certain classes of drugs. Scientists in the pharmaceutical and nutritional industries use dissolution testing equipment to determine bioavailability, i.e., the rate at which active ingredients in drug forms become available to be used by the body. Bioavailability testing by this method is required throughout the pharmaceutical manufacturing process to ensure product quality and stability. Other, non-pharmaceutical applications for dissolution testing exist, as well.

Dissolution testing is typically performed using test equipment that holds a plurality of vessels and submerges the vessels in a temperature-controlled dissolution bath. Each vessel is then filled with a dissolution medium in which a solute is placed, e.g., in a mesh basket. The dissolution medium is then stirred using a stirring element, e.g., a rotating paddle. The stirring elements and baskets corresponding to each of the vessels are typically collectively mounted on a single drive head, so that they can be raised or lowered in unison. At some point, one or more samples of the resulting solution are taken from the vessel and evaluated, e.g., using a spectrophotometer, either in situ or by transporting the samples to an external device. Once testing is complete, the vessels are usually transported to a sink or other station for cleaning, which involves draining, washing, and sometimes drying the vessels. Once cleaning is complete, and prior to re-use of the vessels for subsequent testing, the precise location and centering of each vessel and the height adjustment of the stirring element must be verified. Each time a vessel is replaced after cleaning, this verification process needs to be repeated to maintain consistent and accurate parameters. Depending on the number of vessels, the cleaning and verification processes can be tedious, time-consuming, and inefficient.

SUMMARY OF THE INVENTION

Problems in the prior art are addressed in accordance with the principles of the present invention by providing a dissolution vessel washing system that permits in-situ cleaning of dissolution vessels.

In one embodiment, a vessel washer (e.g., 100) comprises: a nozzle assembly (e.g., 214) comprising a nozzle (e.g., 203) and having formed therein a rinse passageway (e.g., 245) and a waste passageway (e.g., 247), each passageway having first and second ends. The first end of the waste passageway is adapted to be coupled to a waste pump adapted to remove waste fluid via a waste aperture (e.g., 248) defining the second end of the waste passageway. The first end of the rinse passageway is coupled to a rinse pump adapted to provide rinse fluid via a rinse aperture (e.g., 246) defining the second end of the rinse passageway. The nozzle is coupled to the rinse aperture and is adapted to rotate and direct flow of the rinse fluid outwardly while rotating.

In another embodiment, a vessel washer (e.g., 100) comprises a nozzle assembly (e.g., 214) comprising a shaft (e.g., 206) and a drain tip (e.g., 205) slidably disposed within the shaft, and having formed therein a rinse passageway (e.g., 245) and a waste passageway (e.g., 247), each passageway having first and second ends. The first end of the waste passageway is adapted to be coupled to a waste pump adapted to remove waste fluid via a waste aperture (e.g., 248) formed in the drain tip and defining the second end of the waste passageway. The first end of the rinse passageway is adapted to be coupled to a rinse pump adapted to provide rinse fluid via a rinse aperture (e.g., 246) defining the second end of the rinse passageway.

In still another embodiment, a vessel washer (e.g., 100) comprises a nozzle assembly (e.g., 214) comprising a shaft (e.g., 206), a drain tip (e.g., 205) slidably disposed within the shaft and having formed therein a rinse passageway (e.g., 245) and a waste passageway (e.g., 247), each passageway having first and second ends, a nozzle (e.g., 203) and a ball bearing (e.g., 237). A rinse pump is coupled to a first end of the rinse passageway and adapted to provide rinse fluid via a rinse aperture (e.g., 246) defining the second end of the rinse passageway. A waste pump is coupled to a first end of the waste passageway and adapted to remove waste fluid via a waste aperture (e.g., 248) defining the second end of the waste passageway, the drain tip being biased in the direction of the waste aperture. A gasket (e.g., 201) is adapted to contact the upper surface of a vessel, sealingly disposing the nozzle assembly in the vessel. A plurality of vessel holders (e.g., 217) are radially-disposed and outwardly-biased, each vessel holder having a groove (e.g., 228) on an outer surface, such that the plurality of vessel holders are adapted to receive an o-ring (e.g., 202), wherein the o-ring circumferentially retains the plurality of vessel holders. A rinse wand (e.g., 113) is adapted to provide rinse fluid from the rinse pump. A waste tank is coupled to the waste pump, for storing waste fluid. A rinse tank is coupled to the rinse pump, for storing rinse fluid. The nozzle is coupled to the rinse aperture and is adapted to rotate and direct flow of the rinse fluid outwardly while rotating. The flow of the rinse fluid from the nozzle is unobstructed by any portion of the vessel washer. The flow of rinse fluid provided via the rinse aperture causes the nozzle to rotate. The nozzle has at least one slot (e.g., 251) formed in an upper portion thereof and at least one slot (e.g., 252) formed in a lower portion thereof. The ball bearing is disposed in the waste passageway and biased toward the waste aperture to reduce or prevent backflow of waste fluids from the waste passageway out of the waste aperture. At least one tank has a sight level gauge (e.g., 111, 112) permitting visual inspection of the tank fluid level.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 8 is a side perspective view of the nozzle of FIG. 4;

FIG. 9 is a cross-sectional view of the nozzle of FIG. 4 taken along plane E-E of FIG. 8;

DETAILED DESCRIPTION

Figure 1:
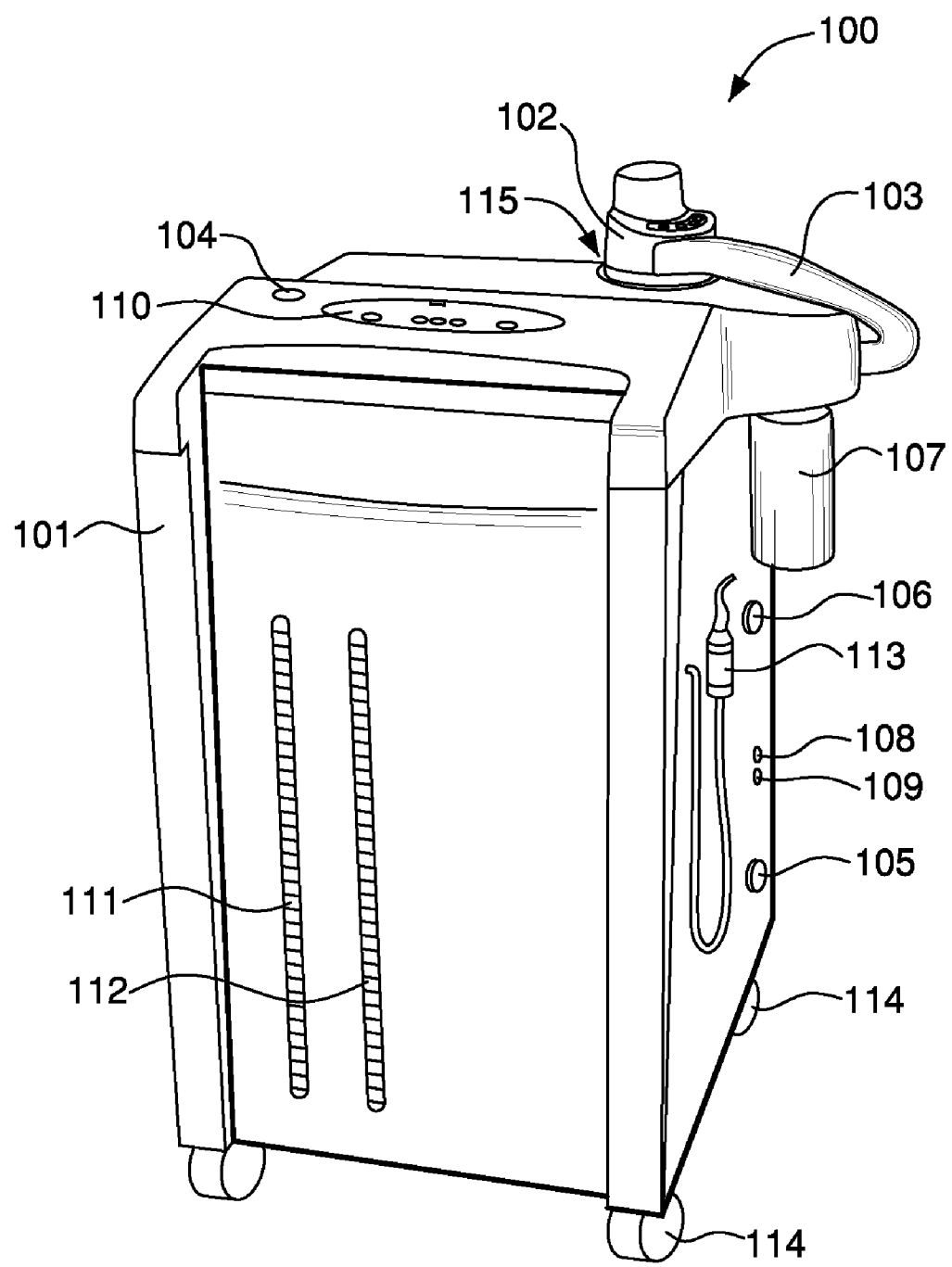
FIG. 1 is a perspective view of an exemplary vessel washer consistent with one embodiment of the present invention.

FIG. 1 illustrates an exemplary vessel washer 100 consistent with one embodiment of the present invention. As shown, vessel washer 100 comprises a housing 101, a wash assembly 102, a sleeve 103, quick-connect ports 104, 105, 106, a particulate trap 107, buttons 108, 109, a user interface 110, external sight gauges 111, 112, rinse wand 113, and wheels 114. While not visible in FIG. 1, a waste tank coupled to a waste pump and a rinse tank coupled to a rinse pump are disposed within housing 101, and a heater may be used to heat the rinse medium in the rinse tank.

Housing 101 has a recessed cradle portion 115 formed in the top surface thereof, for receiving and storing wash assembly 102 when wash assembly 102 is not in use. Wash assembly 102 is a hand-held unit that contains components for coupling to and washing (i.e., rinsing and draining) a vessel. Wash assembly 102 is coupled to one end of sleeve 103, the other end of which is coupled to housing 101. Sleeve 103 is a sheath that contains tubing (e.g., clear PVC) through which the rinse pump can provide a rinse medium from the rinse tank to wash assembly 102 and tubing (e.g., clear PVC) through which the waste pump can extract waste fluids from a vessel being cleaned, to be stored in the waste tank. Sleeve 103 may also contain one or more electrical and/or optical conductors through which various input, output and/or control signals can be exchanged between a secondary user interface 211 (best seen in FIG. 10) disposed on or in wash assembly 102 and various internal components of vessel washer 100 disposed within housing 101.

Quick-connect port 104 is disposed in the top surface of housing 101 for filling the rinse tank. Quick-connect port 105 is disposed in a side panel of housing 101 for draining the rinse tank (e.g., by coupling to an external drain sleeve). Quick-connect port 106 is disposed in a side panel of housing 101 for draining the waste tank (e.g., by coupling to an external drain sleeve). While not visible in FIG. 1, a drain waste pump may be provided to assist in draining the waste tank. Particulate trap 107, which prevents buildup of sediment in the waste tank, is removably coupled to housing 101 and comprises, e.g., a mesh screen or other filtering device. Buttons 108, 109 disposed on housing 101 may be provided to initiate draining of the rinse tank and waste tank, respectively. User interface 110, which is disposed on or in the top surface of housing 101, permits control of various wash parameters, e.g., wash cycle selection and the temperature of the rinse medium. User interface 110 may also permit monitoring of the status of system components, e.g., the levels of the waste tank and the rinse tank. Internal electronic level sensors (not shown) may be provided for each tank, and external sight gauges 111, 112 (although shown on the front side of housing 101, these sight gauges may be disposed within any of the side panels of housing 101) to permit a user to verify visually the levels of the waste tank and the rinse tank. Wheels 114 may be provided to move vessel washer 100 near the dissolution test vessel(s) being washed.

Rinse wand 113 may be provided to permit a user to rinse various dissolution test equipment components, such as stirring elements, shafts, baskets, and/or paddles. These components may be rinsed prior to washing the corresponding dissolution vessel in which the components were disposed. This may be done, e.g. by raising the shafts, rinsing the shafts, paddles, and/or baskets with the wand so that the rinse medium drips into the vessels below. This process is repeated for each of the shafts, paddles, and/or baskets, and the drive head is then raised. Subsequently, each of the vessels, in turn, may be cleaned using wash assembly 102.

Figure 2:
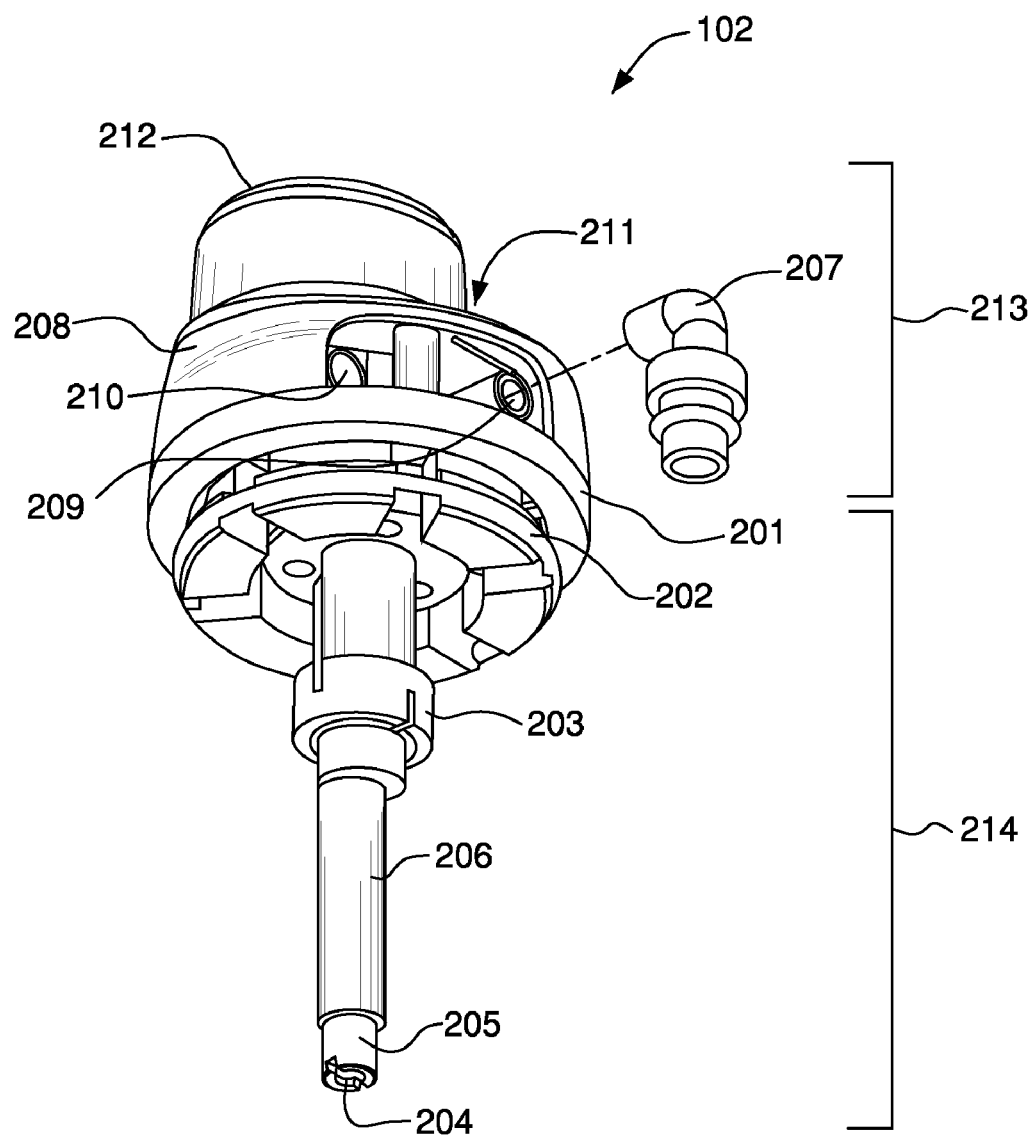
FIG. 2 is a perspective view of a wash assembly in the vessel washer of FIG. 1.

FIG. 2 illustrates wash assembly 102 of FIG. 1, which comprises a gasket 201, an o-ring 202, a rotating nozzle 203, a drain port 204, a drain tip 205, a shaft 206, an elbow fitting 207, and a cover 208. As will be explained in further detail below, gasket 201 (constructed of, e.g., foam) sealingly rests on top of the opening of a vessel being washed, and o-ring 202 is outwardly biased and elastic and fits within the opening of the vessel being washed. The expansion and contraction of o-ring 202 permits wash assembly to be "universal" or "self-adjusting," i.e., sealingly engaging wash assembly 102 with the openings of vessels of varying diameters, thereby permitting a user to operate vessel washer 100 in a hands-free manner, without having to hold wash assembly 102 in place. Nozzle 203 provides a rinse medium to the inside of the vessel for cleaning, and drain port 204 removes waste fluids from inside the vessel. Drain tip 205 is slidably disposed within shaft 206 and is biased in the direction of drain port 204. This configuration permits wash assembly 102 to be used with vessels of varying heights by locating drain port 204 closely adjacent the bottom of a vessel being washed. Elbow fitting 207, which projects from an aperture 209 in cover 208, is connected to one end of a first length of tubing (not shown) disposed inside sleeve 103 of FIG. 1, where the other end of the tubing is connected to the rinse pump within vessel washer 100. Aperture 210 formed in cover 208 is configured to receive another elbow fitting 233 (best seen in FIG. 4), which is connected to one end of a second length of tubing (not shown) disposed inside sleeve 103, where the other end of the tubing is connected to the waste pump within vessel washer 100. Cover 208 may have a secondary user interface 211 (best seen in FIG. 10) disposed on or in a surface thereof, for control of wash parameters and monitoring of system component status. The control and monitoring functionality of secondary user interface 211 may be the same as, similar to, or different from the functionality provided by user interface 110 and may be used, e.g., to permit remote initiation of a wash operation. Cover 208 has a raised "grip" portion 212 to provide an ergonomic surface for a user to pick up wash assembly 102, insert wash assembly 102 into a vessel, remove wash assembly 102 from a vessel, and replace wash assembly 102 into cradle portion 115.

Figure 3:
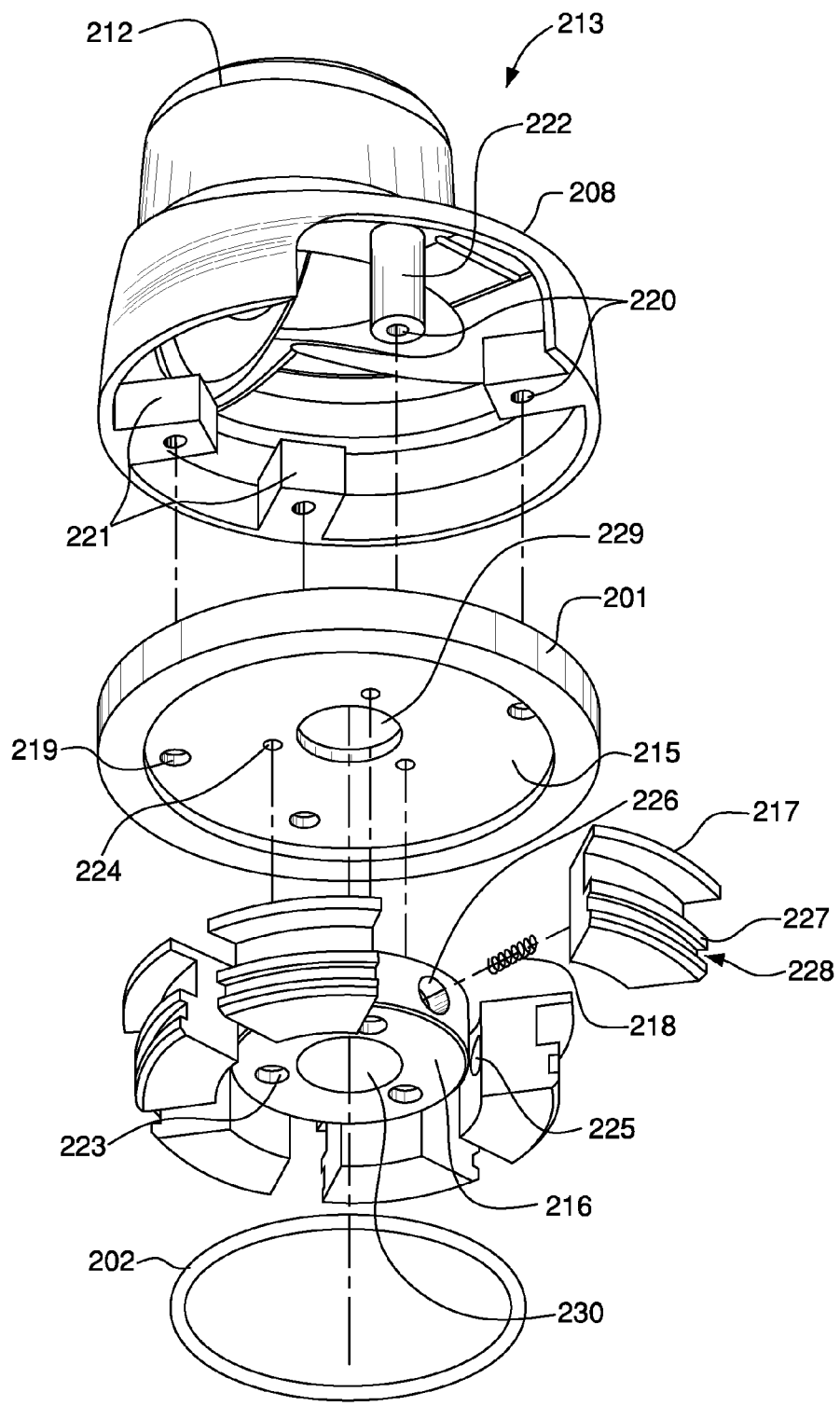
FIG. 3 is an exploded view of the outer assembly of the wash assembly of FIG. 2.
Figure 4:
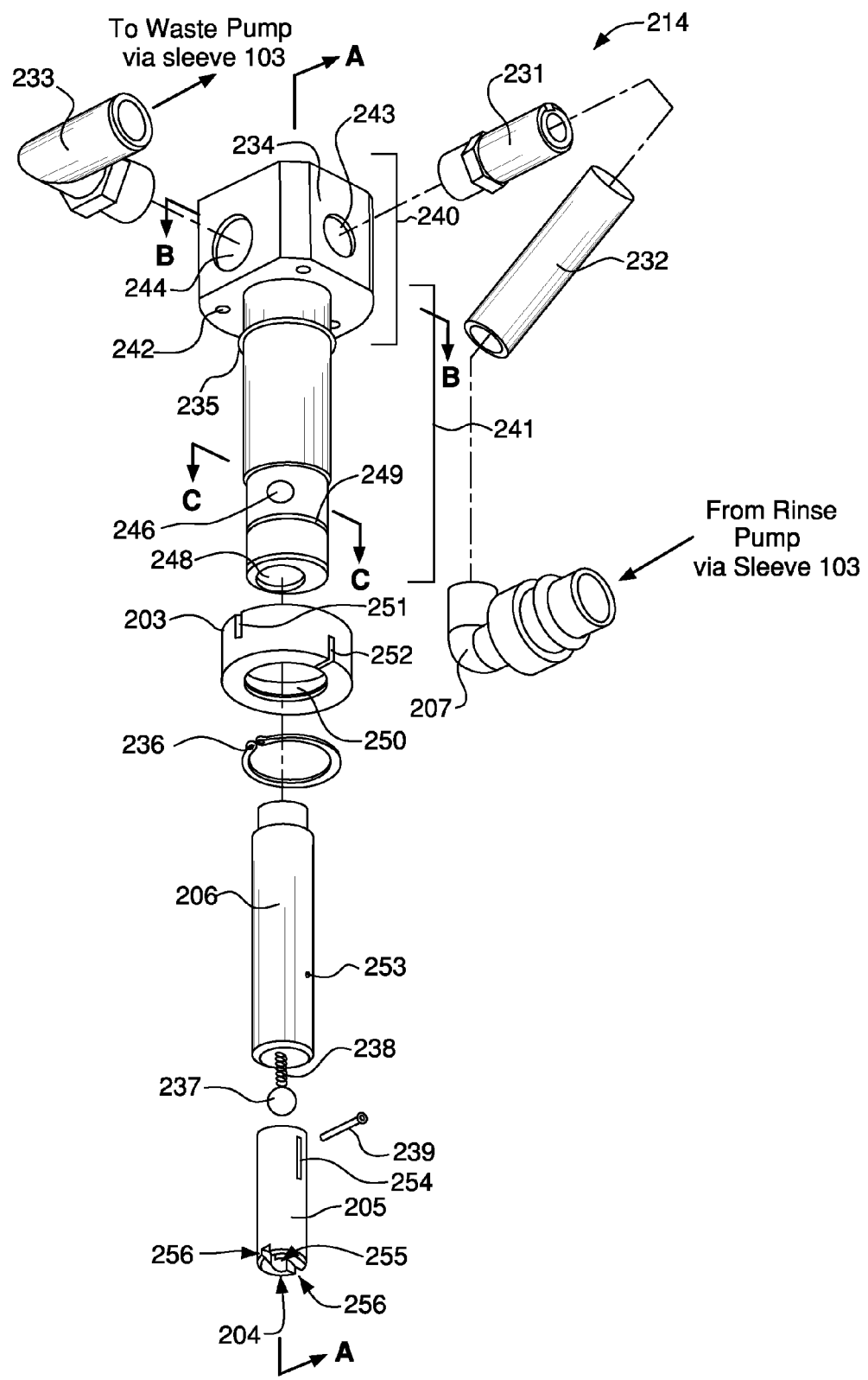
FIG. 4 is an exploded view of the inner assembly of the wash assembly of FIG. 2.

FIGS. 3 and 4 illustrate in exploded views the details of vessel cover assembly 213 and nozzle assembly 214, respectively, of wash assembly 102 of FIG. 2. With reference to FIG. 3, vessel cover assembly 213 comprises a vessel cover 215 having an aperture 229 centrally formed therein, gasket 201, cover 208, a vessel cover 215, a vessel holder connector 216 having an aperture 230 centrally formed therein, a set of six wedge-shaped vessel holders 217, springs 218, and o-ring 202. Vessel cover 215 is coupled to gasket 201 and is secured to cover 208 by a set of four screws (not shown) inserted through screw holes 219 formed in vessel cover 215 and threadably secured into tapped screw holes 220 formed in rectilinear blocks 221 (mounted on or formed in the inner side wall of cover 208) and cylindrical boss 222 (mounted on or formed in an inner top wall of cover 208). Vessel holder connector 216, which is secured to vessel cover 215 by a set of three screws (not shown) inserted into screw holes 223 formed in vessel holder connector 216, through screw holes 242 formed in nozzle pilot 234 (best seen in FIG. 4), and threadably secured into tapped screw holes 224 formed in vessel cover 215, also has a set of cylindrical recesses 226 formed in the outer surface thereof.

Each of vessel holders 217 has a cylindrical recess 225 formed therein that aligns with a respective recess 226 formed in vessel holder connector 216. Each of vessel holders 217 is coupled to vessel holder connector 216 by a spring 218 received by recesses 226 and 225, where spring 218 outwardly biases its respective vessel holder 217. Each of vessel holders 217 has one or more ridges 227 and/or grooves 228 formed therein for receiving o-ring 202, which circumferentially retains and inwardly biases vessel holders 217. Thus, while spring 218 outwardly biases vessel holders 217, o-ring 202 limits the outward travel of vessel holders 217, and the inward travel of vessel holders 217 is limited by contact with the outer surface of vessel holder connector 216. The range of inward travel of o-ring 202 (through contraction) and vessel holders 217 is desirably predetermined to correspond to the inner diameter of the opening of the smallest vessel with which vessel washer 100 is to be used. Likewise, the range of outward travel of o-ring 202 (through expansion) and vessel holders 217 is desirably predetermined to correspond to the inner diameter of the opening of the largest vessel with which vessel washer 100 is to be used. Accordingly, o-ring 202 is adapted to engage sealingly the opening of any vessel within the size range and to permit hands-free operation of wash assembly 102.

With reference now to FIG. 4, nozzle assembly 214 comprises elbow fitting 207, a fitting adapter 231, a length of tubing 232, elbow fitting 233, a nozzle pilot 234, rotating nozzle 203, an o-ring 235, a retainer clip 236, shaft 206, a ball bearing 237, a spring 238, drain tip 205, and a dowel pin 239. Elbow fitting 207 is coupled to the rinse pump and rinse tank via tubing (not shown) disposed within sleeve 103. Elbow fitting 207 is also coupled to tubing 232, which is coupled to fitting adapter 231. Elbow fitting 233 is coupled to the waste pump and waste tank via tubing (not shown) disposed within sleeve 103. Some or all of the foregoing tubing connections may be made, e.g., using a nylon sleeve clamp (not shown) and/or by interference fit. Nozzle pilot 234 has upper portion 240 and lower portion 241. Upper portion 240 is secured to vessel cover 215 and vessel holder connector 216 by the screws (not shown) passing through screw holes 242. Lower portion 241 projects through aperture 229 (best seen in FIG. 3) centrally formed in vessel cover 215 and aperture 230 (best seen in FIG. 3) centrally formed in vessel holder connector 216. Nozzle assembly 214 is secured to vessel cover assembly 213 by means of the screws passing through screw holes 242 and the projection of lower portion 241 through apertures 229 and 230. O-ring 235 is disposed around nozzle pilot 234, between upper portion 240 and lower portion 241 and engages vessel cover 215 to form a seal between upper portion 241 of nozzle pilot 234 and the upper surface of vessel cover 215.

Figure 5:
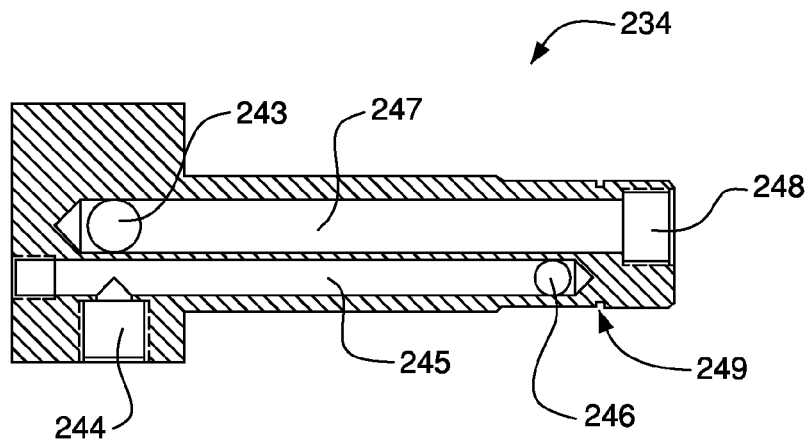
FIG. 5 is a cross-sectional view of the nozzle pilot of FIG. 4 taken along plane A-A of FIG. 4.
Figure 6:
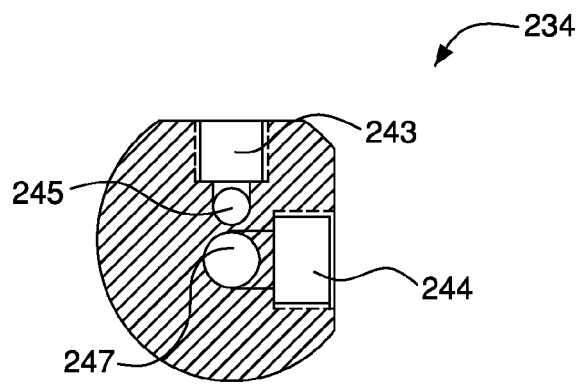
FIG. 6 is a cross-sectional view of the nozzle pilot of FIG. 4 taken along plane B-B of FIG. 4.
Figure 7:
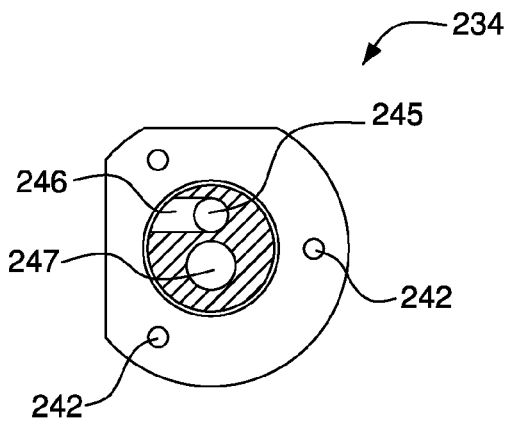
FIG. 7 is a cross-sectional view of the nozzle pilot of FIG. 4 taken along plane C-C of FIG. 4.

Nozzle pilot 234 has apertures 243, 244 formed therein for receiving fitting adapter 231 and elbow fitting 233, respectively, which may be welded or otherwise fastened to nozzle pilot 234 therethrough. With reference now to FIG. 5 (a cross-sectional view of nozzle pilot 234 taken along plane A-A of FIG. 4), FIG. 6 (a cross-sectional view of nozzle pilot 234 taken along plane B-B of FIG. 4), and FIG. 7 (a cross-sectional view of nozzle pilot 234 taken along plane C-C of FIG. 4), it can be seen that aperture 243 defines one end of a rinse passageway 245 extending through lower portion 241 of nozzle pilot 234, where channel 246 defines the other end of rinse passageway 245. Aperture 244 defines one end of a waste passageway 247 extending through lower portion 241 of nozzle pilot 234, where aperture 248 defines the other end of waste passageway 247. As shown, rinse passageway 245 is offset from center to accommodate adjacent waste passageway 247.

Returning now to FIG. 4, rotating nozzle 203 is an annular nozzle having an inner diameter sized to receive lower portion 241 of nozzle pilot 234 slidably and rotatably therein. Nozzle 203 is retained along lower portion 241 of nozzle pilot 234 from traveling downward by means of retainer clip 236, which snaps into groove 249 formed in nozzle pilot 234. Nozzle 203 has an inner diameter slightly larger than the outer diameter of lower portion 241 of nozzle pilot 234, thereby permitting rotating nozzle 203 to rotate about lower portion 241 of nozzle pilot 234.

FIG. 8 is a detailed view of rotating nozzle 203, and FIG. 9 is a cross-sectional view of rotating nozzle 203 taken along plane E-E of FIG. 8. As shown, rotating nozzle 203 has a groove 250 formed along the inner circular walls thereof, two upper nozzle slots 251 formed in opposing sides of the upper surface thereof, and two lower nozzle slots 252 formed in opposing sides of the lower surface thereof. Upper nozzle slots 251 are offset with respect to lower nozzle slots 252 by 90°. Nozzle 203 communicates with channel 246 of nozzle pilot 234, such that when the rinse pump provides a rinse medium through rinse passageway 245 via channel 246, channel 246 directs the flow at an angle (best seen in FIG. 7) that causes the flow to circulate within groove 250 in either a clockwise or a counter-clockwise direction. The circulating flow within groove 250 provides torque to drive the rotation of nozzle 203 in the direction of circulation of the flow. While nozzle 203 rotates, nozzle 203 outwardly directs the spray of the rinse medium. In particular, the flow exits rotating nozzle 203 via upper nozzle slots 251 and lower nozzle slots 252 formed therein, so as to direct the spray of the rinse medium both upwardly and downwardly onto the inner surfaces of the vessel being washed. Thus, over time, the rotation of nozzle 203 permits the rinse medium to be sprayed directly onto substantially all of the inner surfaces of the vessel in an unobstructed manner, for thorough cleaning.

Returning now to FIG. 4, shaft 206 has a substantially cylindrical passageway formed therein and is secured within aperture 248 of nozzle pilot 234 (e.g., by interference fit or threaded connection). Drain tip 205 is slidably disposed within the cylindrical passageway of shaft 206 and is biased toward drain port 204 by means of spring 238. The inward travel of spring 238 is restricted by a stop (not shown) formed inside shaft 206, and the outward travel of spring 238 is restricted by ball bearing 237, which spring 238 biases toward drain port 204 to close drain port 204 when the waste pump is not operating. When the waste pump is operating and applies negative pressure to drain port 204, ball bearing 237 retracts. Thus, ball bearing 237 operates as a check valve to prevent or reduce the backflow of waste fluid out of drain port 204 into the dissolution vessel following a draining operation. Dowel pin 239 is disposed through aperture 253 formed in shaft 206 and slot 254 formed in drain tip 205, thereby limiting the range of slidable travel of drain tip 205 within shaft 206. Drain port 204 communicates with aperture 248 via the passageway of shaft 206, such that, when the waste pump applies negative pressure to the waste passageway, waste fluids from a vessel being washed are removed through drain port 204. In addition to its central opening 255 to permit removal of waste located directly underneath drain port 204, drain port 204 has two side openings 256 to permit removal of waste located adjacent the bottom portion of drain tip 205.

Exemplary materials from which the various components of vessel washer 100 may be constructed are as follows. Vessel holders 217, vessel holder connector 216, vessel cover 215, drain tip 205, shaft 206, rotating nozzle 203, and nozzle pilot 234 are constructed from polyvinyl chloride (PVC). Elbow fitting 233 and fitting adapter 231 are constructed from high-density polyethylene, and elbow fitting 207 is constructed from polypropylene. Dowel pin 239, retainer clip 236, spring 238, ball bearing 237, and the screws used to connect the various components are constructed from stainless steel. O-ring 235 is constructed from rubber. Cover 208 is constructed from Kydex T (an acrylic/PVC thermoplastic sheet material manufactured by Kleerdex Company of Bloomsburg, Pa., USA). Sleeve 103 is constructed from a braided sleeving comprising polyethylene terephthalate filaments.

Figure 10:
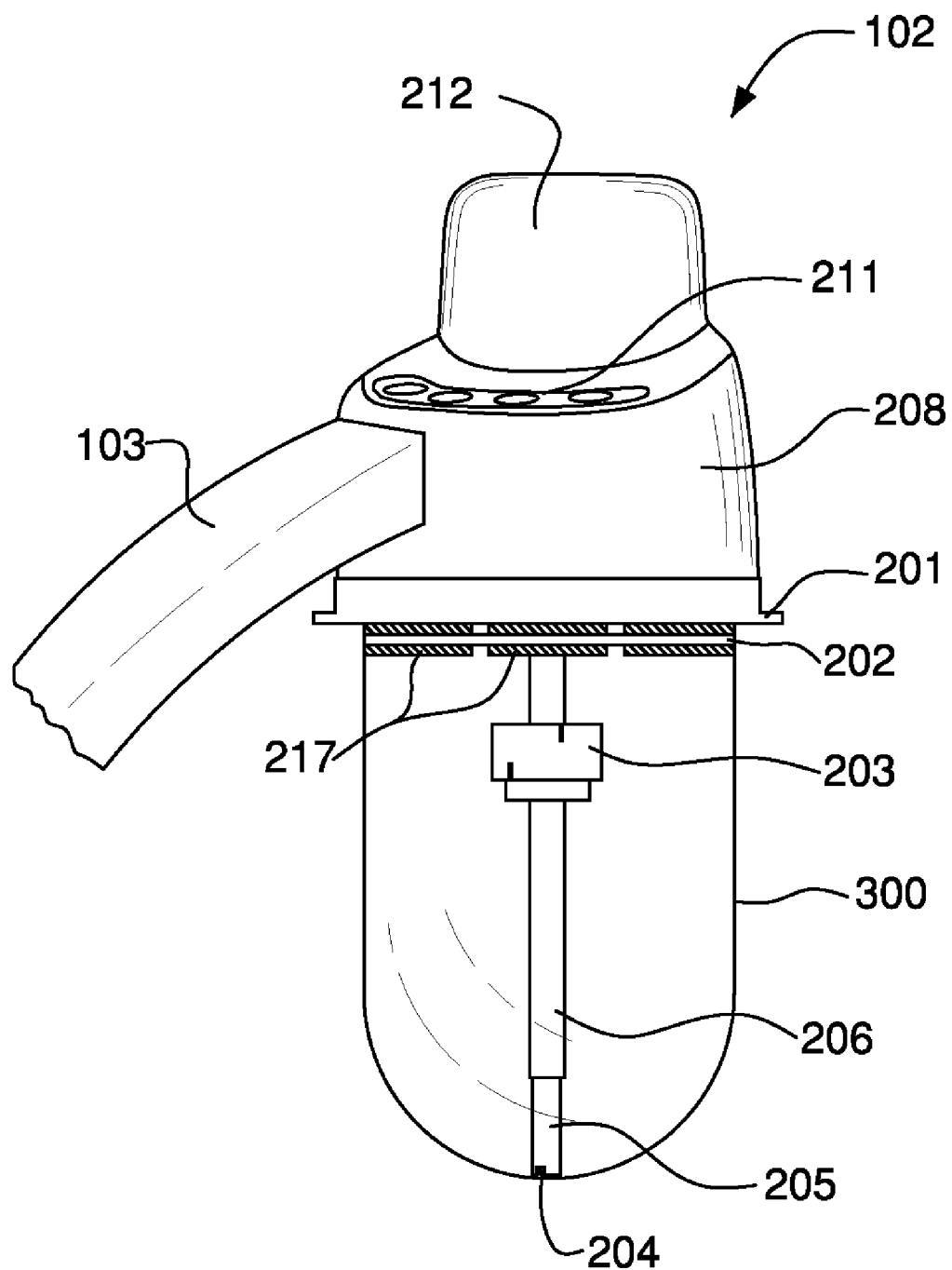
FIG. 10 shows the wash assembly of FIG. 2 engaged with a vessel in an exemplary cleaning operation.

FIG. 10 shows wash assembly 102 engaged with a transparent dissolution test vessel 300 in an exemplary cleaning operation. During rinse operations, the rinse pump supplies the rinse medium from the rinse tank to wash assembly 102, which emits the rinse medium from rotating nozzle 203. During drain operations, the waste pump removes waste fluids from the vessel and provides the waste fluids to the waste tank. The spray from rotating nozzle 203 impinges on the interior surface of the vessel, rinsing it, and the rinse medium collects in the bottom of the dissolution vessel, where it is removed by the drain. The rotation of nozzle 203 causes the rinse medium to exhibit centrifugal force within the vessel and creates a cyclone effect, which is intensified by the application of negative pressure at the drain when draining and rinsing are simultaneously performed.

In an exemplary wash cycle, the pumps are operated by a controller (not shown) to automatically perform rinse and drain operations. In such automatic operation, the pumps may be operated so that during a first interval, fluid remaining from a test is withdrawn from the dissolution vessel through the drain. During a second interval, the rinse medium is delivered to the nozzle to spray the interior surface of the dissolution vessel, and the rinse medium collecting in the bottom of the dissolution vessel is removed (either contemporaneously or subsequently) through the drain. During a third interval, the delivery of the rinse medium to the nozzle is stopped, and residual rinse medium collecting in the bottom of the dissolution vessel is subsequently removed through the drain. The inside of the vessel may then be wiped clean, if necessary, prior to reuse. Various automatic wash operations are possible, including, e.g., light, medium, and heavy wash cycles, and manual rinsing and draining Phases of a programmable wash cycle can include, e.g., alternating between draining and rinsing (e.g., a preset number of times) or draining and rinsing simultaneously. Circuitry (not shown) may be provided to indicate audibly to a user of the vessel washer that the end of a programmed cycle has been reached.

Figure 11:
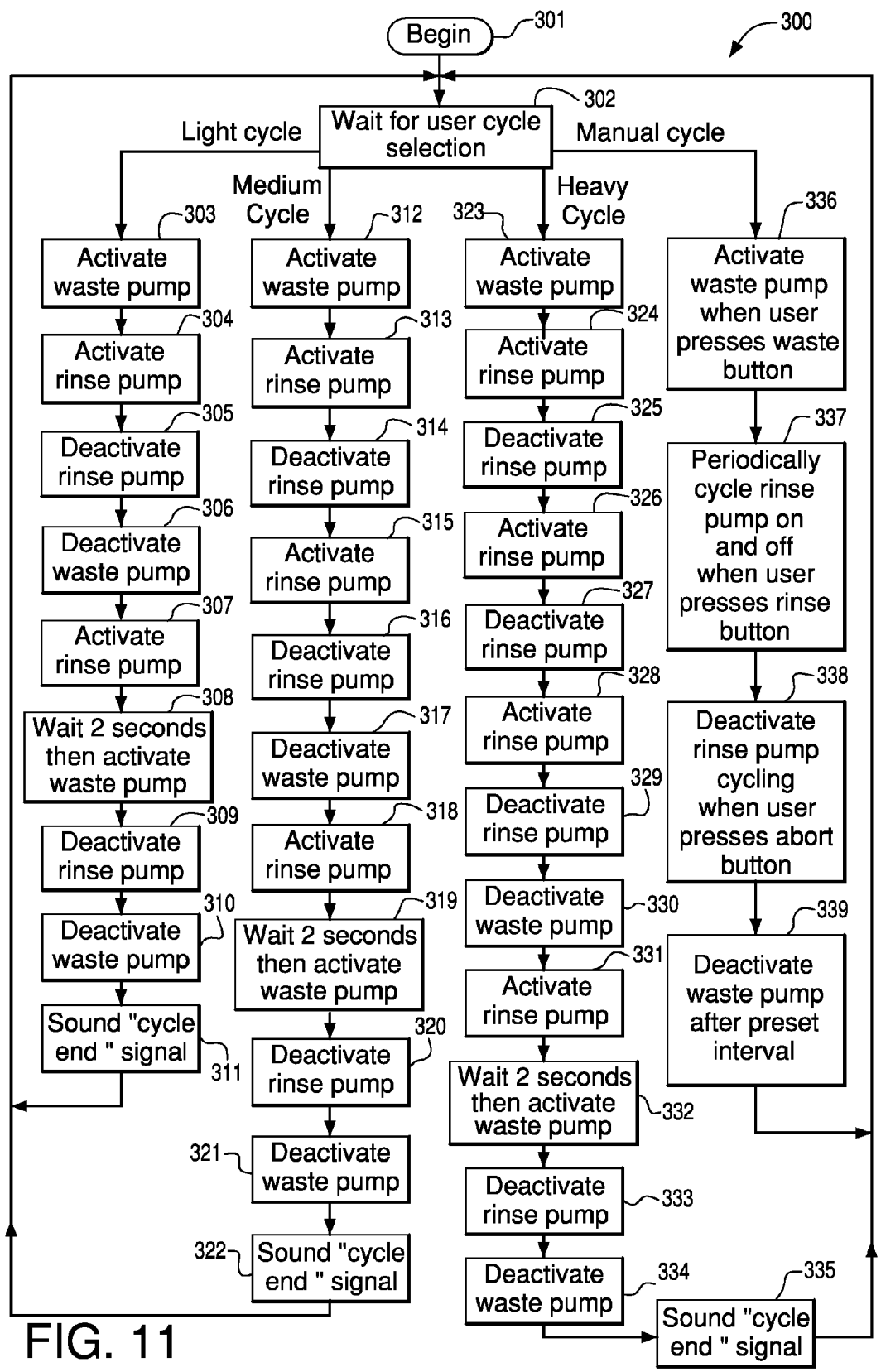
FIG. 11 shows a process flow for an exemplary control program of the vessel washer of FIG. 1.

FIG. 11 shows a process flow 300 for an exemplary control program of vessel washer 100. The process begins at block 301. At block 302, a user selects a light cycle, medium cycle, heavy cycle, or manual cycle. If the user selects a light cycle, then the process continues at block 303. If the user selects a medium cycle, then the process continues at block 312. If the user selects a heavy cycle, then the process continues at block 323. If the user selects a manual cycle, then the process continues at block 336.

If, at block 302, the user has selected a light cycle, then, at block 303, the waste pump is activated to drain from the vessel the bulk of any standing waste fluid, i.e., typically a dissolution medium after the vessel has been used for a dissolution test. The waste pump will stay activated through the end of the cycle. At block 304, the rinse pump is activated to cause the nozzle to spray the rinse medium to rinse downwardly any remaining waste fluid on the walls of the vessel, so that the waste fluid is removed by the waste pump via drain tip 205. At block 305, the rinse pump is deactivated to permit drainage of any standing waste fluid from the bottom of the vessel. At block 306, the waste pump is deactivated temporarily, to permit accumulation of rinse fluid in the bottom of the vessel in the subsequent step. At block 307, the rinse pump is once again activated to cause the nozzle to spray the rinse medium to rinse downward any remaining waste fluid on the walls of the vessel. At block 308, after a preselected delay (e.g., 2 seconds), the waste pump is once again activated, so that the waste fluid is removed by the waste pump via drain tip 205. At block 309, the rinse pump is deactivated to permit drainage of any standing waste fluid from the bottom of the vessel. At block 310, the waste pump is deactivated, and the cleaning cycle is complete. At block 311, an "end of cycle" signal is sounded to alert the user that the cycle is complete, and the process continues at block 302 to wait to receive another selection from the user.

If, at block 302, the user has selected a medium cycle, then, at block 312, the waste pump is activated to drain from the vessel the bulk of any standing waste fluid. The waste pump will stay activated through the end of the cycle. At blocks 313 through 316, the rinse pump alternates twice between being activated to rinse downward any remaining waste fluid on the walls of the vessel and deactivated to permit the waste drainage of any standing waste fluid from the bottom of the vessel. At block 317, the waste pump is deactivated temporarily, to permit accumulation of rinse fluid in the bottom of the vessel in the subsequent step. At block 318, the rinse pump is once again activated to cause the nozzle to spray the rinse medium to rinse downward any remaining waste fluid on the walls of the vessel. At block 319, after a preselected delay (e.g., 2 seconds), the waste pump is once again activated, so that the waste fluid is removed by the waste pump via drain tip 205. At block 320, the rinse pump is deactivated to permit drainage of any standing waste fluid from the bottom of the vessel. At block 321, the waste pump is deactivated, and the cleaning cycle is complete. At block 322, an "end of cycle" signal is sounded to alert the user that the cycle is complete, and the process continues at block 302 to wait to receive another selection from the user.

If, at block 302, the user has selected a heavy cycle, then, at block 323, the waste pump is activated to drain from the vessel the bulk of any standing waste fluid. The waste pump will stay activated through the end of the cycle. At blocks 324 through 329, the rinse pump alternates three times between being activated to rinse downward any remaining waste fluid on the walls of the vessel and deactivated to permit the waste drainage of any standing waste fluid from the bottom of the vessel. At block 330, the waste pump is deactivated temporarily, to permit accumulation of rinse fluid in the bottom of the vessel in the subsequent step. At block 331, the rinse pump is once again activated to cause the nozzle to spray the rinse medium to rinse downward any remaining waste fluid on the walls of the vessel. At block 332, after a preselected delay (e.g., 2 seconds), the waste pump is once again activated, so that the waste fluid is removed by the waste pump via drain tip 205. At block 333, the rinse pump is deactivated to permit drainage of any standing waste fluid from the bottom of the vessel. At block 334, the waste pump is deactivated, and the cleaning cycle is complete. At block 335, an "end of cycle" signal is sounded to alert the user that the cycle is complete, and the process continues at block 302 to wait to receive another selection from the user.

If, at block 302, the user has selected a manual cycle, then, at block 336, once the user presses a "waste" button, the waste pump is activated to drain from the vessel the bulk of any standing waste fluid. The waste pump will stay activated until the user presses an "abort" button. At block 337, once the user presses a "rinse" button, the rinse pump begins to cycle on and off to rinse downward any remaining waste fluid on the walls of the vessel, so that the waste fluid is removed by the waste pump via drain tip 205. At block 338, once the user presses the "abort" button, the rinse pump cycling is deactivated to permit drainage of any standing waste fluid from the bottom of the vessel. At block 339, after a preselected interval to account for the time required to permit drainage of any standing waste fluid from the bottom of the vessel, the rinse pump is deactivated. The process continues at block 302 to wait to receive another selection from the user.

Thus, the present invention permits cleaning of dissolution test vessels in situ, without the need for removing the vessels and relocating them to a separate cleaning station or sink Advantageously, the use of a single integral nozzle assembly 214 that can be inserted into a vessel, with (1) the nozzle being able to rotate 360° near the top of the vessel and (2) the drain located centrally at the bottom of the vessel, eliminates the problem of "dead zones," i.e., over time, the rinse medium can be directly applied to substantially all of the inner surfaces of the vessel without interference that would be caused by the use of a non-rotating nozzle and/or a separate drain tube.

Although the vessel washer is described herein as having utility in the cleaning of dissolution test vessels, it should be understood that the present invention may also have utility in cleaning other types of vessels and other devices.

It will be further understood that various changes in the details, materials, and arrangements of the parts which have been described and illustrated in order to explain the nature of this invention may be made by those skilled in the art without departing from the scope of the invention as expressed in the following claims.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

Although the steps in the following method claims, if any, are recited in a particular sequence with corresponding labeling, unless the claim recitations otherwise imply a particular sequence for implementing some or all of those steps, those steps are not necessarily intended to be limited to being implemented in that particular sequence.

We claim:

1. A vessel washer comprising:
a nozzle assembly comprising a nozzle and having formed therein a rinse passageway and a waste passageway, each passageway having first and second ends;
wherein:
the first end of the waste passageway is configured to be coupled to a waste pump adapted to remove waste fluid via a waste aperture defining the second end of the waste passageway;
the first end of the rinse passageway is coupled to a rinse pump configured to provide rinse fluid via a rinse aperture defining the second end of the rinse passageway; and
the nozzle is coupled to the rinse aperture and is configured to rotate around the waste passageway and direct flow of the rinse fluid outwardly while rotating.

2. The invention of claim 1, wherein the flow of the rinse fluid from the nozzle is unobstructed by any portion of the vessel washer.

3. The invention of claim 1, wherein the flow of rinse fluid provided via the rinse aperture causes the nozzle to rotate.

4. The invention of claim 3, wherein the nozzle has at least one slot formed in an upper portion thereof and at least one slot formed in a lower portion thereof.

5. The invention of claim 1, wherein the nozzle assembly comprises a shaft and a drain tip slidably disposed within the shaft, and the waste aperture is formed in the drain tip.

6. The invention of claim 5, wherein the drain tip is biased to travel, relative to the shaft, in the direction of the waste aperture.

7. The invention of claim 1, further comprising a ball bearing disposed in the waste passageway and biased toward the waste aperture to reduce or prevent backflow of waste fluids from the waste passageway out of the waste aperture.

8. The invention of claim 1, wherein the nozzle assembly further comprises a gasket adapted to contact the upper surface of a vessel, sealingly disposing the nozzle assembly in the vessel.

9. The invention of claim 1, wherein the nozzle assembly further comprises a plurality of radially-disposed and outwardly-biased vessel holders.

10. The invention of claim 9, wherein each vessel holder has a groove on an outer surface, such that the plurality of vessel holders are adapted to receive an o-ring, wherein the o-ring circumferentially retains the plurality of vessel holders.

11. A nozzle assembly for a vessel washer comprising:
a nozzle having formed therein a rinse passageway and a waste passageway, each passageway having first and second ends;
wherein:
the first end of the waste passageway is configured to be coupled to a waste pump adapted to remove waste fluid via a waste aperture defining the second end of the waste passageway;
the first end of the rinse passageway is coupled to a rinse pump configured to provide rinse fluid via a rinse aperture defining the second end of the rinse passageway; and
the nozzle is coupled to the rinse aperture and is configured to rotate around the waste passageway and direct flow of the rinse fluid outwardly while rotating.

12. The invention of claim 11, wherein the flow of the rinse fluid from the nozzle is unobstructed by any portion of the vessel washer.

13. The invention of claim 11, wherein the flow of rinse fluid provided via the rinse aperture causes the nozzle to rotate.

14. The invention of claim 13, wherein the nozzle has at least one slot formed in an upper portion thereof and at least one slot formed in a lower portion thereof.

15. The invention of claim 11, further comprising a shaft and a drain tip slidably disposed within the shaft, wherein the waste aperture is formed in the drain tip.

16. The invention of claim 15, wherein the drain tip is biased to travel, relative to the shaft, in the direction of the waste aperture.

17. The invention of claim 11, further comprising a ball bearing disposed in the waste passageway and biased toward the waste aperture to reduce or prevent backflow of waste fluids from the waste passageway out of the waste aperture.

18. The invention of claim 11, further comprising a gasket adapted to contact the upper surface of a vessel, sealingly disposing the nozzle assembly in the vessel.

19. The invention of claim 11, further comprising a plurality of radially-disposed and outwardly-biased vessel holders.

20. The invention of claim 19, wherein each vessel holder has a groove on an outer surface, such that the plurality of vessel holders are adapted to receive an o-ring, wherein the o-ring circumferentially retains the plurality of vessel holders.

* * * * *